United States Patent
Fine et al.

(10) Patent No.: US 7,025,869 B2
(45) Date of Patent: Apr. 11, 2006

(54) NITRIC OXIDE DELIVERY SYSTEM

(75) Inventors: David H. Fine, Lincoln, MA (US); Stephen J. MacDonald, Salem, NH (US); David Rounbehler, West Harwich, MA (US); David Wheeler, Lunenburg, MA (US); Jonathan L. Rolfe, N. Easton, MA (US); George Jarvis, Arlington, MA (US)

(73) Assignee: CyTerra Corporation, Waltham, MA (US)

( * ) Notice: Subject to any disclaimer, the term of this patent is extended or adjusted under 35 U.S.C. 154(b) by 375 days.

(21) Appl. No.: 10/229,026

(22) Filed: Aug. 28, 2002

(65) Prior Publication Data

US 2003/0064115 A1 Apr. 3, 2003

(51) Int. Cl.
*C25B 1/22* (2006.01)
*A61M 16/00* (2006.01)
*A01D 59/00* (2006.01)

(52) U.S. Cl. ............ 205/553; 128/204.18; 128/204.21; 424/718

(58) Field of Classification Search ................ 205/553; 128/204.18, 204.21; 424/718
See application file for complete search history.

(56) References Cited

U.S. PATENT DOCUMENTS

| | | | |
|---|---|---|---|
| 1,021,234 A * | 3/1912 | Muller von Berneck et al. | 205/553 |
| 4,010,897 A | 3/1977 | Treharne et al. | 239/8 |
| 4,287,040 A | 9/1981 | Alamaro | 204/179 |
| 4,774,069 A | 9/1988 | Handley | 423/403 |
| 4,778,450 A | 10/1988 | Kamen | 604/65 |
| 5,396,882 A | 3/1995 | Zapol | 128/200.14 |
| 5,485,827 A | 1/1996 | Zapol et al. | 128/200.14 |
| 5,525,357 A | 6/1996 | Keefer et al. | 424/486 |
| 5,545,614 A | 8/1996 | Stamler et al. | 514/6 |
| 5,558,083 A | 9/1996 | Bathe et al. | 128/203.12 |
| 5,570,683 A | 11/1996 | Zapol | 128/200.14 |
| 5,615,669 A | 4/1997 | Olsson et al. | 128/203.12 |
| 5,651,358 A | 7/1997 | Briend et al. | 128/203.12 |
| 5,676,963 A | 10/1997 | Keefer et al. | 424/423 |
| 5,683,668 A | 11/1997 | Hrabie et al. | 423/405 |
| 5,692,495 A | 12/1997 | Sheu | 128/203.12 |
| 5,823,180 A | 10/1998 | Zapol | 128/200.24 |
| 5,827,420 A * | 10/1998 | Shirazi et al. | 205/220 |
| 5,839,433 A | 11/1998 | Higenbottam | 128/204.21 |
| 5,871,009 A | 2/1999 | Rydgren et al. | 128/203.12 |
| 5,873,359 A | 2/1999 | Zapol et al. | 128/203.12 |
| 5,994,444 A | 11/1999 | Trescony et al. | 524/429 |

(Continued)

FOREIGN PATENT DOCUMENTS

WO WO 94/16740 8/1994

(Continued)

OTHER PUBLICATIONS

Suzuki, "Nitrogen Oxides Generation Method for Recovered Nitric Acid by Electrolysis. An Action Plan for Reduction of Low-Level-Liquid-Waste in Processing Plant", Kyoto Daigaku Genshiro Jikkensho, (Tech. Rep.) (no month, 1991), KURRI-TR-361, pp. 19-26.*

(Continued)

*Primary Examiner*—Edna Wong
(74) *Attorney, Agent, or Firm*—Fish & Richardson P.C.

(57) ABSTRACT

Inhalation of low levels of nitric oxide can rapidly and safely decrease pulmonary hypertension in mammals. Precise delivery of nitric oxide at therapeutic levels of 20 to 100 ppm and inhibition of reaction of nitric oxide with oxygen to form toxic impurities such as nitrogen dioxide can provide effective inhalation therapy for pulmonary hypertension.

17 Claims, 1 Drawing Sheet

U.S. PATENT DOCUMENTS

| | | | | |
|---|---|---|---|---|
| 6,103,275 | A | * | 8/2000 | Seitz et al. .................. 424/718 |
| 6,109,260 | A | | 8/2000 | Bathe .................... 128/203.12 |
| 6,158,434 | A | | 12/2000 | Lugtigheid et al. .... 128/204.22 |
| 6,190,704 | B1 | | 2/2001 | Murrell ...................... 424/718 |
| 6,261,594 | B1 | | 7/2001 | Smith et al. ................ 424/445 |
| 6,270,779 | B1 | | 8/2001 | Fitzhugh et al. ............ 424/400 |
| 6,758,214 | B1 | | 7/2004 | Fine et al. ............. 128/203.12 |

FOREIGN PATENT DOCUMENTS

| | | |
|---|---|---|
| WO | WO 01/15738 A2 | 3/2001 |

OTHER PUBLICATIONS

Pulfer, Sharon Kay. "Nitric Oxide Releasing Polymers and Their Application to Vascular Devices (Polyethyleneimine, Polytetrafluoroethylene)", *Dissertation Abstracts International.* vol. 56 12-B, pp 6727 (1995)*.

Roselle, Dominick C., et al., "Characterization and Nitric Oxide Release Studies of Lipophilie 1-Substituted Diazen-1-ium-1,2-Diolates", *Journal of Controlled Release,* vol. 51, pps 131-142 (1998)*.

Smith, Daniel J.,et al., "Nitric Oxide-Releasing Polymers Containing the [N(O)NO]Group", *Journal of Medicinal Chemistry,* vol. 39, No. 5, pps. 1148-1156 (1996), no month.

Taira, Masafumi, et al. "Continuous Generation System for Low-Concentration Gaseous Nitrous Acid", *Analytical Chemistry,* vol. 62, No. 6, pps. 630-633 (1990), no month.

International Search Report, 8 pages, Mar. 10, 2004.

* cited by examiner

NITRIC OXIDE DELIVERY SYSTEM

CLAIM OF PRIORITY

This application claims the benefit of U.S. Application No. 60/316,964 filed on Sep. 5, 2001, which is incorporated by reference in its entirety.

CROSS REFERENCE TO RELATED APPLICATIONS

The present application is related to co-pending application Ser. No. 10/228,958, entitled "Method and Apparatus For Generation of Nitric Oxide," and co-pending application Ser. No. 10/228,956, entitled "Controlled Generation of Nitric Oxide," each of which was filed on Aug. 28, 2002, and is incorporated by reference in its entirety.

TECHNICAL FIELD

This invention relates to an apparatus and a method for controllably generating nitric oxide.

BACKGROUND

Nitric oxide plays an important role in the regulation of biochemical pathways in living organisms. The inhalation of low levels (20 to 100 ppm) of nitric oxide has been shown to have a major therapeutic value in treatment of a diverse range of disorders ranging from reversible and irreversible pulmonary hypertension to treatment of neonates exhibiting hypoxemic respiratory failure and persistent pulmonary hypertension. Conventional medical uses of nitric oxide gas can involve dilution of a nitric oxide gas stream with gases immediately before administration of the nitric oxide gas to a mammal. Precise delivery of nitric oxide at therapeutic levels of 20 to 100 ppm and inhibition of reaction of nitric oxide with oxygen to form toxic impurities such as nitrogen dioxide gas is needed for effective inhalation therapy.

SUMMARY

Nitric oxide, also known as nitrosyl radical, is a free radical that is an important signaling molecule in pulmonary vessels. Nitric oxide can moderate pulmonary hypertension caused by elevation of the pulmonary arterial pressure. Inhaling low concentrations of nitric oxide, for example, in the range of 20–100 ppm can rapidly and safely decrease pulmonary hypertension in a mammal by vasodilation of pulmonary vessels.

Some disorders or physiological conditions can be mediated by inhalation of nitric oxide. The use of low concentrations of inhaled nitric oxide can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide can also be used to treat chronic pulmonary hypertension, bronchopulmonary dysplasia, chronic pulmonary thromboembolism and idiopathic or primary pulmonary hypertension or chronic hypoxia. Advantageously, nitric oxide can be generated and delivered in the absence of harmful side products, such as nitrogen dioxide. The nitric oxide can be generated at a concentration suitable for delivery to a mammal in need of treatment.

A nitric oxide delivery system can be a controlled drug delivery system, which produces steady-state levels of nitric oxide. The system can provide for zero-order, first order or second order drug release kinetics. Controlled drug delivery devices can provide a constant level of pharmaceutical drug to a mammal which can optimize the drug input rate into the systemic circulation, improve mammal compliance, minimize side effects, and maximize drug product efficacy.

Controlled nitric oxide delivery can include controlling the diffusion/dissolution of the nitric oxide. The nitric oxide precursor composition can include a matrix and a contained phase of a nitric oxide precursor, for slow or controlled release of nitric oxide into the surrounding or external medium. Controlling the release of nitric oxide can result in greater longevity of the nitric oxide precursor and longer availability of the nitric oxide precursor for its intended purpose while providing a means for greater control in the concentration of nitric oxide into the surrounding medium.

In one aspect, a method of delivering nitric oxide to a mammal includes disposing a cathode and an anode in a solution of a nitric oxide precursor, applying a voltage across the cathode and anode to generate nitric oxide substantially devoid of nitrogen dioxide, contacting a transport gas with the solution of nitric oxide precursor to form a therapeutic gas; and transporting the therapeutic gas in the transport gas to a mammal. The nitric oxide precursor can be a precursor salt. The precursor salt can be an alkali metal nitrite, alkali metal nitrate, alkaline earth metal nitrite, alkaline earth metal nitrate or ammonium nitrate. The concentration of the precursor salt can be between 0.1% to 20%. The nitric oxide precursor can be potassium nitrite, sodium nitrite, rubidium nitrite, strontium nitrite, barium nitrite, calcium nitrite, copper nitrite, zinc nitrite, potassium nitrate, sodium nitrate, rubidium nitrate, strontium nitrate, barium nitrate, calcium nitrate, copper nitrate and zinc nitrate. The nitric oxide precursor can be, for example, sodium nitrite. The therapeutic gas can include 20 to 60 ppm of nitric oxide. The transport gas can be oxygen, ambient air or a mixture of air and oxygen. The transport gas can be ambient air which can flow over or through the solution of nitric oxide precursor and can transport the therapeutic gas for at least one hour. The therapeutic gas can be substantially devoid of nitrogen dioxide.

In another aspect, a method of delivering nitric oxide from an electrochemical cell to a mammal includes disposing a cathode and an anode in a solution of dilute nitric acid, the anode including copper, applying a voltage across the cathode and the anode to generate nitric oxide substantially devoid of nitrogen dioxide; contacting a transport gas through the solution of dilute nitric acid to form a therapeutic gas including the nitric oxide and transporting the therapeutic gas to the mammal. The dilute nitric acid can be at least 0.5 M.

In another aspect, a kit includes a nitric oxide precursor and instructional material describing a method of generating a therapeutic gas and transporting the therapeutic gas. The therapeutic gas can include nitric oxide and can be substantially devoid of nitrogen dioxide.

Other features or advantages will be apparent from the following detailed description of several embodiments, and also from the appended claims.

DETAILED DESCRIPTION

Figure 1:
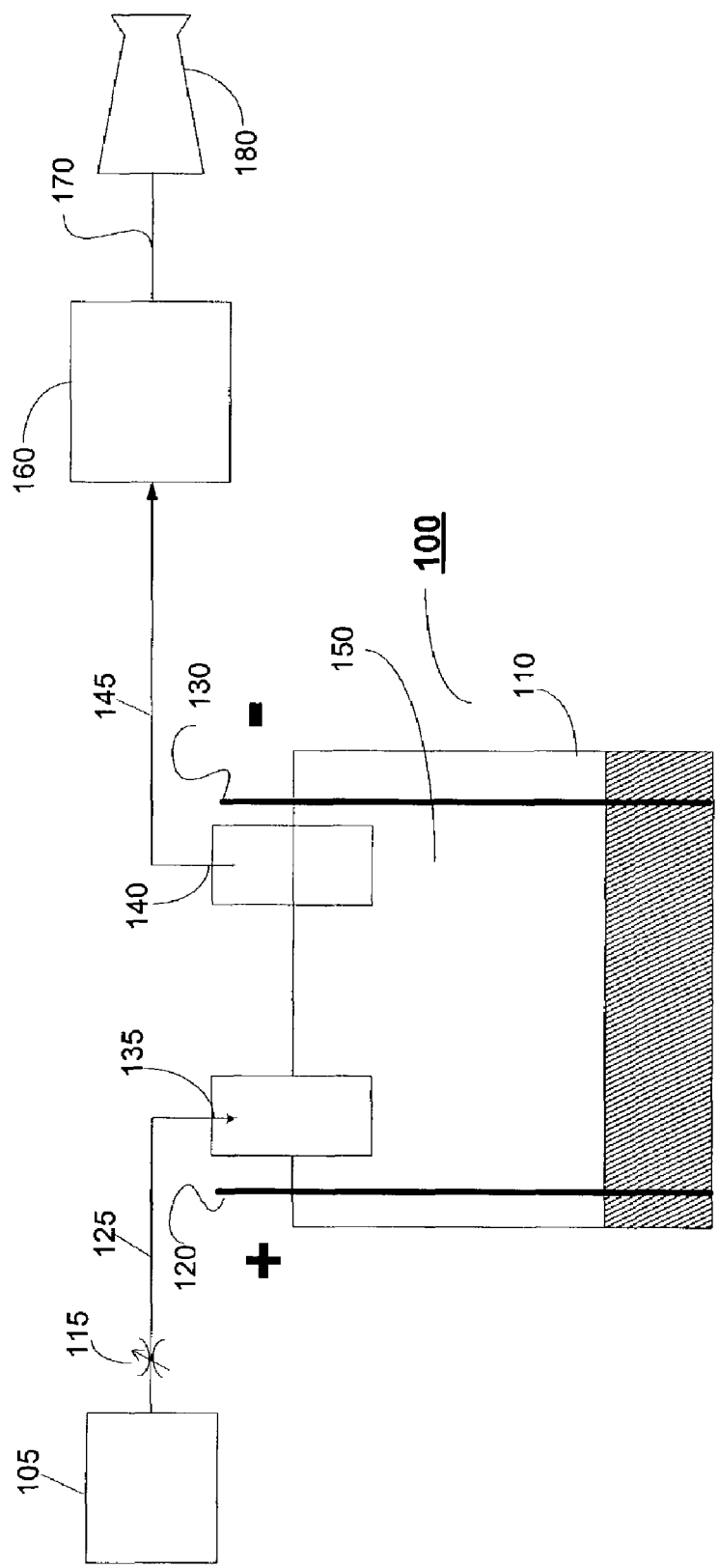
FIG. 1 is a drawing depicting a schematic view of a nitric oxide generation and delivery system.

Various nitric oxide precursors can be used in a nitric oxide delivery system. Nitric oxide precursors can include a nitrogen-containing compound with a structure X-Nitric Oxide, when X is an organic residue or a precursor salt. For example, the nitric oxide precursor can include an alkali metal nitrite, an alkaline earth metal nitrite, a transition metal nitrite or an ammonium nitrite, for example, potassium nitrite, sodium nitrite, rubidium nitrite, strontium nitrite, barium nitrite, calcium nitrite, copper nitrite, zinc nitrite, or mixtures thereof. The nitric oxide precursor can include nitrogen-containing acids, such as nitric acid. Physical characteristics of the nitric oxide precursor, such as the dissolution rate, can be used to control delivery of nitric oxide.

The nitric oxide precursor can be dissolved in a solution in which the precursor can dissociate to form anions, including nitrite anions, and cations. The solution can include a buffer solution. A buffer solution can include a pH buffer combination which is a solution containing either a weak acid or a weak base at a concentration that renders the solution resistant to change in pH. The buffer solution provides a source of hydrogen cations, which can combine with the nitrite anions to form nitrous acid ($HNO_2$). Nitrous acid can decompose into several products in water. One of these products is nitric oxide. The reactions are summarized below in equations (I), (II) and (III):

$$NaNO_2 \leftrightarrow Na^+ + NO_2^- \quad (I)$$

$$NO_2^- + H^+ \leftrightarrow HNO_2 \quad (II)$$

$$3HNO_2 \leftrightarrow H_2O + H^+ + NO_3^- + 2NO \quad (III)$$

The nitric oxide precursor can include sodium nitrite, which dissociates into sodium cations and nitrite anions, as shown in equation (I). The nitrite anions in the buffer solution can form nitrous acid as shown in equation (II), which can decompose into water, nitrate and hydrogen ions and two molecules of gaseous nitric oxide, as shown in equation (III).

The generated nitric oxide gas formed by the above reactions has a low solubility in the pH buffer combination (e.g., 0.00983 g nitric oxide per liter at 0° C.; 4.6 mL/100 mL at 20° C. in water (Merck Index, 10th Edition, 1983)). The relatively insoluble nitric oxide can be removed from the solution by a transport gas stream to form a therapeutic gas. The transport gas can be 100% oxygen, a mixture of air and oxygen or ambient air. The transport gas stream can be bubbled, otherwise distributed through the solution or swept over the solution. Other byproducts such as, for example, nitrous acid and nitrogen dioxide, can be volatile and can be carried with the transport gas stream along with nitric oxide formed in the reaction.

When delivering nitric oxide for therapeutic use to a mammal, it can be important to avoid delivery of nitrogen dioxide to the mammal. Nitrogen dioxide can be formed by the oxidation of nitric oxide with oxygen. The rate of formation of nitrogen dioxide is proportional to the square power of the nitric oxide concentration and the single power of the oxygen concentration. Reducing the nitric oxide concentration by a factor of ten reduces the nitrogen dioxide concentration by a factor of one hundred. Thus, by limiting the nitric oxide concentration in a therapeutic gas, the therapeutic gas can be substantially devoid of nitrogen dioxide. For example, when nitric oxide concentration in the transport gas is below 100 ppm, the resulting therapeutic gas generated from the nitric oxide precursor in a solution is substantially devoid of nitrogen dioxide.

In certain circumstances, the concentration of nitric oxide generated in the therapeutic gas is controlled, for example, by the concentration of nitric oxide precursor provided to the solution, the concentration of hydrogen cations in the solution, and the characteristics of the pH buffer combination. Other factors that can affect the nitric oxide concentration in the therapeutic gas can include, for example, physical form of the nitric oxide precursor, presence of a reduction-oxidation reaction in an optional gas purifier, and rate of flow of the transport gas through the solution.

The concentrations of hydrogen cations and the nitric oxide precursor can control the rate of generation of nitric oxide. Since the concentration of nitric oxide is low, about 20 to 100 ppm, reaction conditions, that increase the concentration of nitric oxide precursor and decrease the concentration of hydrogen ions lead to a stoichiometrically inefficient reaction. Decreasing the concentration of hydrogen ions, for example, by using a weak acid, shifts the equilibrium in equation (II) toward the nitrite anions. A reservoir of nitrite ions can be created such that the nitrous acid concentration is maintained at a relatively constant level.

A kit includes the nitric oxide precursor and an instructional material describing a method of generating the therapeutic gas and transporting the therapeutic gas in the transport gas. The therapeutic gas including nitric oxide is substantially devoid of impurities such as nitrogen dioxide.

A therapeutic gas can contain at least 1 ppm of nitric oxide. The therapeutic gas can include less than 100 ppm of nitric oxide. For example, the nitric oxide concentration in the therapeutic gas can be from 20 to 100 ppm. The nitric oxide can be released from the precursor over a period of time ranging from 1 minute to 7 days, 2 days to 3 days, or two hours to twenty four hours.

Oxidation-reduction reactions can assist in the production of nitric oxide. For example, a second salt, such as a nitric oxide-releasing reactant, can be added to the solution. A nitric oxide-releasing reactant, for example, an iodide salt or ferrous salt, assists the production of nitric oxide as shown below:

$$2NO_2^- + 2I^- + 4H^+ \rightarrow I_2 + 2H_2O + 2NO$$

or $$2NO_2^- + 2Fe^{+2} + 6e^- \rightarrow 2Fe^{+3} + 2H_2O + 2NO$$

For example, the nitric oxide-releasing reactant can be 1 molar ferrous sulfate solution or 10% wt/wt aqueous solution of sodium iodide.

Controlled-release delivery systems can include chemical reactions, for example, generation of nitric oxide by an electrochemical cell. For example, the reaction of potassium nitrite and potassium nitrate with chromium oxide forms potassium chromate and nitric oxide. This reaction can be controlled to generate nitric oxide.

$$3KNO_2 + KNO_3 + Cr_2O_3 \rightarrow 2K_2CrO_4 + 4NO.$$

Alternatively, nitric oxide can be generated, for example, by the chemical reduction reactions. Metallic copper, for example, and dilute nitric acid can react to generate nitric oxide. For every six electrons transferred, three copper cations are reduced and two molecules of NO gas are generated. The reaction is shown below:

Referring to FIG. 1, a nitric oxide generation and delivery system 100 includes a pump 105 with a restrictor valve 115, an electrochemical cell 110 with a cathode 120, an anode 130, an inlet tube 125, an inlet 135, an outlet tube 145, an outlet 140 and a headspace 150. The cell 110 is connected to an optional gas purifier 160, a tube 170 and a mask 180. The cell 110 is filled with a weak aqueous solution of nitric oxide precursor salt. The position of the anode and cathode in the cell can be modified.

In a general process for generating a stream of nitric oxide, the cathode 120 and anode 130 are immersed in the aqueous solution of nitric oxide precursor and the headspace 150 can be flushed with the transport gas. Alternatively, the transport gas can be bubbled through the solution. Various nitric oxide precursors can be used in the nitric oxide delivery system as described above. The concentration of the precursor salt can be 0.1% to 50%, 0.5% to 35%, or 1% to 20% by weight. A voltage is applied between the cathode and anode to generate the nitric oxide. The transport gas is swept over the solution of nitric oxide precursor to generate nitric oxide. The nitric oxide generated can be transported with the transport gas stream as a therapeutic gas to an optional gas purifier 160. The optional gas purifier 160 removes any impurities such as nitrogen dioxide and nitrous acid as well as any other residual impurities, if present, as described above. The purified therapeutic gas can be transported through tube 170 to mask 180 to the mammal. Several parameters affect the production of nitric oxide in this process. The reaction conditions, for example, electrode material, applied voltage, applied current and nitric oxide precursor concentration can be controlled to generate 10 to 100 ppm of NO in the therapeutic gas.

In certain circumstances, the therapeutic gas can be passed through an optional therapeutic gas purifier 160. When the therapeutic gas stream contacts the optional therapeutic gas purifier, residual impurities, such as nitrous acid and nitrogen dioxide, are removed from the therapeutic gas stream. The optional gas purifier can include a filter, which can be, for example, a semi-permeable membrane or barrier, a scrubbing solution, a reduction-oxidation solution, or a pyrolizer. The semi-permeable membrane is a barrier which allows the nitric oxide and transport gas to pass and retains the impurities. The scrubbing solution is a solution that removes impurities by neutralizing them, for example, a solution of 10% sodium bicarbonate, a 1M ferrous salt solution or an acidified 1M ferrous sulfate solution. A series of aqueous reservoirs can be used to completely decompose the nitrous acid and dissolve any nitric acid or nitrogen dioxide impurities. The reduction-oxidation solution contains a reduction-oxidation agent, which converts impurities completely into nitric oxide. The reduction-oxidation agent can include a ferrous salt. The pyrolizer is a chamber or other component which decomposes the impurities such as nitrous acid and nitrogen dioxide by irradiation or heating. A catalyst, for example, platinum, nickel or silver, can be used to decrease the pyrolysis temperature. For example, the impurities such as nitrous acid and nitrogen dioxide can be passed through a 12 inch long silver tube, 1/8 inch in diameter, heated at 800° C. at a flow rate of 1 L/minute. The removal of impurities can be enhanced by using a convoluted or a long path for the bubbling of the therapeutic gas stream through the filter. Additionally, the surface-to-volume ratio of the bubbles can be increased for effective filtration of impurities. For example, a gas sparger can be used to make smaller bubbles. Alternatively, filter media can also be coated onto a filter or walls of a tube, which can produce a dry therapeutic gas stream upon filtration.

A detector can be included in the therapeutic gas delivery system to detect the concentration of nitric oxide in the therapeutic gas stream. The detector can also detect the concentration of nitrogen dioxide in the therapeutic gas, if necessary, and may provide a warning if the nitric oxide concentration is outside a predetermined range or if the concentration of nitrogen dioxide is above a threshold value. Examples of monitoring techniques include chemiluminescence and electrochemical techniques, and are discussed in, for example, in Francoe et al., "Inhaled nitric oxide: Technical Aspects of Administration and Monitoring," *Critical Care Medicine*, 24(4):782–796 (1998), which is incorporated by reference in its entirety. The presence of nitric oxide can be detected by for example, a modified version of a Thermo-Electron chemiluminescence (CL) detector.

Another design variation which achieves controlled-release delivery includes delivery of nitric oxide by reaction of copper in a dilute nitric acid solution, the nitric oxide precursor, in which case anode 130 can include copper and cell 110 can be filled with, for example, an aqueous solution of dilute nitric acid as the nitric oxide precursor. The dilute nitric acid can be at least 0.5M in concentration of nitric acid in water. Unexpectedly, the nitric oxide generated as a therapeutic gas is free of impurities such as nitrogen dioxide and nitrous acid.

The following examples describe nitric oxide generation.

EXAMPLE 1

Referring to FIG. 1, an electrochemical cell was prepared by fitting a 50 mL glass sample jar with a plastic TEFLON lined lid. Holes were drilled in the lid to accommodate the electrodes. The electrodes are immersed in the 1–20% sodium nitrite as a nitric oxide precursor solution and the headspace is swept with the flowing transport gas. A 0.5 to 5 VDC voltage was applied across the cathode and anode. The transport gas swept the generated nitric oxide as therapeutic gas into the optional gas purifier. Depending upon the voltage applied, the nitric oxide precursor concentration and the type of cathode and anode used, nitric oxide levels between 10 and 100 ppm were present in the therapeutic gas.

TABLE 1

| Voltage (volts) | Nitric oxide precursor concentration | Cathode | Anode | ppm of nitric oxide generated in the therapeutic gas |
|---|---|---|---|---|
| 2 | 3% NaNO$_2$ | Nichrome | Nichrome | 10–100 |
| 2 | 1% NaNO$_2$ | Nichrome | Copper | |
| 2 | 20% NaNO$_2$ | Nichrome | Copper | |
| 1–5 | 20% NaNO$_2$ | Nichrome | Copper | |
| 0.5 | 20% NaNO$_2$ | | | 26 |
| 5 | 20% NaNO$_2$ | | | 100 |
| 5 | 1% NaNO$_2$ | | | 10 |
| 5 | 3% NaNO$_2$ | | | 100 |

Other embodiments are within the scope of the following claims.

What is claimed is:

1. A method of delivering nitric oxide to a mammal comprising:
    disposing a cathode and an anode in a solution of a nitric oxide precursor that includes a precursor salt;

applying a voltage across the cathode and anode to generate nitric oxide substantially devoid of nitrogen dioxide;

contacting a transport gas with the solution of nitric oxide precursor to form a therapeutic gas; and transporting the therapeutic gas to a mammal.

2. The method of claim 1 wherein the precursor salt includes a precursor salt concentration between 0.1% to 50%.

3. The method of claim 2 wherein the precursor salt concentration is between 1% and 20%.

4. The method of claim 1 wherein the precursor salt includes an alkali metal nitrite, alkali metal nitrate, alkaline earth metal nitrite, alkaline earth metal nitrate or ammonium nitrate.

5. The method of claim 1 wherein the nitric oxide precursor includes a salt selected from the group consisting of potassium nitrite, sodium nitrite, rubidium nitrite, strontium nitrite, barium nitrite, calcium nitrite, copper nitrite, zinc nitrite, potassium nitrate, sodium nitrate, rubidium nitrate, strontium nitrate, barium nitrate, calcium nitrate, copper nitrate and zinc nitrate.

6. The method of claim 5 wherein the nitric oxide precursor includes sodium nitrite.

7. The method of claim 1 wherein the therapeutic gas includes at least 1 ppm of nitric oxide.

8. The method of claim 1 wherein the therapeutic gas includes less than 100 ppm of nitric oxide.

9. The method of claim 1 wherein the therapeutic gas includes 20 to 60 ppm of nitric oxide.

10. The method of claim 1 wherein transporting the therapeutic gas includes releasing nitric oxide over a period of time from one hour to seven days.

11. The method of claim 1 wherein transporting the therapeutic gas includes releasing nitric oxide over a period of time from two hours to 24 hours.

12. The method of claim 1 wherein transporting the therapeutic gas includes releasing nitric oxide for at least one hour.

13. The method of claim 1 wherein the transport gas includes oxygen.

14. The method of claim 1 wherein the transport gas includes ambient air.

15. The method of claim 1 wherein the transport gas includes an air and oxygen mixture.

16. The method of claim 1 wherein the therapeutic gas is substantially devoid of nitrogen dioxide.

17. The method of claim 1 wherein contacting the transport gas with the solution of nitric oxide precursor includes flowing transport gas over the solution of nitric oxide precursor.

* * * * *